United States Patent [19]
White

[11] 3,992,105
[45] Nov. 16, 1976

[54] METHOD AND APPARATUS FOR REMOTE SALINITY SENSING

[75] Inventor: Peter G. White, Rancho Palos Verdes, Calif.

[73] Assignee: TRW Inc., Redondo Beach, Calif.

[22] Filed: Mar. 10, 1975

[21] Appl. No.: 557,199

[52] U.S. Cl. .............................. 356/118; 356/114; 356/209
[51] Int. Cl.² ........................................ G01J 4/04
[58] Field of Search .......... 356/114, 118, 209, 210, 356/212

[56] References Cited
UNITED STATES PATENTS
| | | | |
|---|---|---|---|
| 3,060,793 | 10/1962 | Wells | 356/118 |
| 3,790,286 | 2/1974 | Kraus | 356/118 |

OTHER PUBLICATIONS
Born, M. and Wolf, E., "Principles of Optics," Pergamon Press, New York, 1959, p. 43.

Primary Examiner—John K. Corbin
Assistant Examiner—Richard A. Rosenberger
Attorney, Agent, or Firm—Daniel T. Anderson; Stephen J. Koundakjian; Donald R. Nyhagen

[57] ABSTRACT

Disclosed is an improved method and apparatus for remote sensing of the salinity of large bodies of water. Intensity values are simultaneously obtained for the horizontally and vertically polarized components of sunlight specularly reflected as a solar glitter pattern at a point on the surface of the body of water where the salinity is known. The aperture of the vertical polarization detection optical system is adjusted so that the signal voltage from that system is equal to that generated from the horizontal polarization detection optical system at that point. A signal whose amplitude corresponds to the change in salinity between another point and that known point on the surface is generated by multiplying the signal from the horizontal polarization detector by a function of the solar zenith angle and dividing the difference between the output from the horizontal polarization detector and a vertical polarization detector by this product.

8 Claims, 3 Drawing Figures

METHOD AND APPARATUS FOR REMOTE SALINITY SENSING

BACKGROUND OF THE INVENTION

A. Field of the Invention

This invention relates to methods and apparatus for the remote measurement of the salinity of large bodies of water.

B. Cross Reference to Related Application

The invention relates to some extent to the invention disclosed and claimed in my co-pending U.S. Pat. Application, Ser. No. 451,391.

C. Description of Prior Art

It is believed that the method and apparatus most closely related to the present invention is that taught in the aforementioned co-pending application. In that method the solar glitter pattern from a body of water is continuously sensed as the sensor moves across the surface, perhaps at satellite height. Since the light will, to a large degree, be polarized upon reflection from the surface, the light received by the sensor is polarization analyzed along each plane, and the intensity of both vertical and horizontal components is detected. For each intensity reading of the vertical components, the fractional change of intensity over all (or a large fixed number of) previous such readings is calculated. The same is done with the intensity readings of the horizontally polarized components. The ratio of each corresponding set of vertical to horizontal changes is calculated. Depending on the solar zenith angle (i.e., 90° minus the elevation angle from the horizon), these ratios will by comparison with theoretical values, indicate which of the intensity changes have resulted from a change in salinity, as opposed to other factors, such as sea state. For each intensity change determined to result from a salinity change, the actual change in salinity is calculated, using formulae derived from the Fresnel equations.

The apparatus described in my co-pending application comprises sensor means to acquire corresponding intensity values for the horizontally and vertically polarized light from the solar glitter pattern. These values are analyzed by means for calculation in accordance with the above-described method.

While this previous invention is adequate to obtain reliable salinity measurements under a wide range of conditions, it possesses certain inherent limitations. One of these is that in order to obtain data from which salinity changes may be calculated, a large number of horizontal and vertical polarization intensity readings must be compared to determine initially which data indicate salinity changes and which indicate light intensity changes caused by other factors such as sea state. Accordingly, in this previous method a large number of calculations must be made to obtain reliable data from which salinity changes may be calculated.

SUMMARY OF THE INVENTION

Accordingly, it is an object of the present invention to provide a method and apparatus for remote salinity measurement which is comparatively simple and straight forward.

In the present invention, separate optical systems are utilized to detect the intensity of the horizontally and vertically polarized components of the light specularly reflected from the glitter pattern. The "vertical" system utilizes a variable aperture, while the "horizontal" system aperture may be fixed. The optical system is calibrated by adjusting the vertical system aperture so that the detector outputs from the horizontal and vertical systems are equal at a point where the salinity is known. Without changing the aperture of the vertical system, the difference between the horizontal and vertical outputs is measured at a calibration point where the salinity is unknown. The horizontal output is multiplied by a function of the solar zenith angle and the aforementioned difference is divided by this product. The quotient is a linear function of the change in salinity between the point corresponding to those measurements and the calibration point.

The apparatus comprises separate optical systems for generating outputs corresponding respectively to the vertically and horizontally polarized components of the light. Means such as a variable aperture are provided in the vertical polarization detection system for the aforementioned initial calibration. Means are provided to input the appropriate value of the function of the solar zenith angle into multipler means for multiplication by the signal generated from the horizontal polarization detection means. Means are provided to generate a difference between the horizontal polarization detection output and the vertical output, and means are provided to divide the signal from the subtraction means by the signal from the multiplication means. The quotient is a linear function of the change in salinity between that point and the calibration point and may be read from any conventional display device such as a volt meter.

DETAILED DESCRIPTION OF PREFERRED EMBODIMENT

The apparatus must provide means for separate intensity measurement of the horizontally and vertically polarized components of the reflected light beam.

Figure 1:
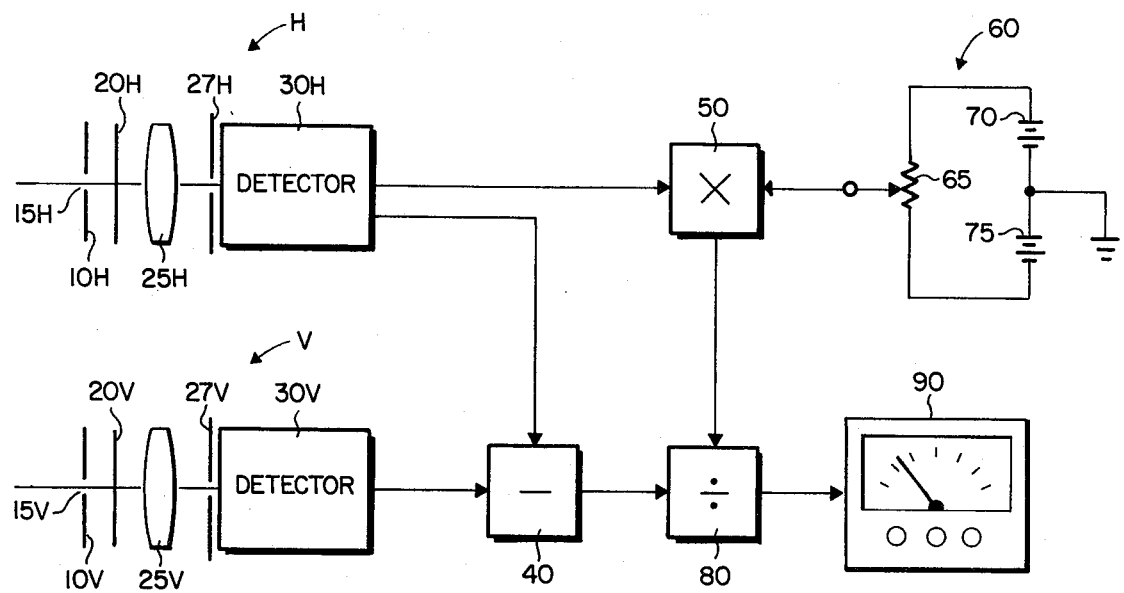
FIG. 1 is a schematic representation of the apparatus according to the preferred embodiment of the present invention.

The simplest and preferred means for accomplishing this is illustrated in FIG. 1.

In the embodiment illustrated, a separate optical device is utilized for each component — each element of the device, H, utilized in measuring the intensity of the horizontal polarized component is shown with the index numerals having a suffix H, while the representation of the "vertical" device, V, utilizes V suffixes. As shown, the two devices are aligned with their optical axes parallel so that each device obtains its readings from the same remote location. In particular, a single housing may be utilized for the pair of optical devices. Such a housing is not illustrated, as it is conventional and forms no part of the invention.

The two devices are, of course, calibrated so that they will exhibit substantially identical sensitivity.

In the preferred embodiment of the apparatus of the present invention, light specularly reflected from the solar glitter pattern on the water surface may be reduced in intensity by neutral density filters (not shown)

before impinging on the detectors. The purpose of this intensity reduction is to avoid saturation of the detectors by the high intensity reflected light beam.

The horizontal polarization component detection device H comprises, in series, an aperture stop 10H having a fixed aperture 15H to allow the passage of light from the solar glitter pattern, a horizontally orientated polarization analyzer 20H, an imaging lens 25H, a field stop 27H and a visible light detector 30H. The horizontal polarization analyzer preferably comprises an ordinary sheet polarizer with its polarization plane oriented horizontally with respect to the water surface being remotely sensed. The detector is an ordinary visible light detection means, preferably a silicon photodiode. The field stop is a circular aperture of sufficient size to define the desired field of view.

An optional element may intervene between the imaging lens 25H and the field stop 27H, onto which the light is imaged. This optional element (not shown) comprises a narrow band (approximately 150 angstrom) filter whose purpose is to narrow the wave length band of the transmitted beam and, thus, to avoid problems which might otherwise arise because of the dependency of the index of refraction of the water on the wave length of the light impinging upon it and reflected from it.

The vertical polarization component detection apparatus V is identical to the horizontal device, except, of course, the vertical analyzer 20V is oriented vertically with respect to the water surface and the aperture 15V is adjustable for reasons which will soon become apparent. The variable aperture may be provided by any conventional means such as an iris.

There are other means by which a pair of beams may be created for separate analysis.

For example, separate analysis of the intensity of the horizontally and vertically polarized components may be made in a single-barrelled instrument. This may be accomplished by placing a rotating analyzer in the path of the beam. As the analyzer's polarization plane rotates, it will alternately pass the horizontally polarized component and the vertically polarized component, as its polarization plane is first aligned with the polarization plane of one and then the other. The intensity of the unpolarized component of the light will undergo a constant attenuation of 50%, caused in a well-known manner by the randomness of the vibration planes of the unpolarized light. Some synchronization means, well within the capacity of the reasonably skilled practitioner, must be included so that the output signal representing the horizontal polarization intensity may be separated from that representing the vertical polarization intensity.

Referring again to the preferred embodiment illustrated in FIG. 1 of the drawing, one of the beams is transmitted through the horizontal polarization analyzer 20H. This will cause horizontally polarized light from the glitter pattern to pass through the analyzer unimpeded, while vertically polarized light is blocked, and unpolarized light is attenuated by 50 %. The transmitted beam continues to the horizontal intensity detector 30H.

The other beam passes through the vertical analyzer 20V whose polarization plane is aligned in perpendicular orientation with respect to that of the first analyzer 20H. The second analyzer will pass unimpeded vertically polarized light, while horizontally polarized light will be blocked, and unpolarized light will be attenuated in intensity by 50%. The transmitted beam is imaged onto the vertical intensity detector 30V.

An analog subtractor 40 receives the outputs from the horizontal detector 30H and the vertical detector 30V. This subtractor, which may comprise an ordinary summing junction, outputs the difference in signal strength between the output from the horizontal detector and the output from the vertical detector.

The instrument which comprises the preferred embodiment of the present invention is calibrated by adjusting the vertical aperture 15V so that the substractor outputs a null signal when the instrument is oriented toward a solar glitter pattern eminating from a point where the salinity is known. Following this calibration the instrument will continue to generate readings which are linearly proportional to the difference in salinity between the successive reading points and this calibration point. The vertical aperture is adjusted in a conventional manner, for example by mechanically opening or closing down and iris diaphragm.

Once the instrument has been thus calibrated, a non-zero output from the subtractor 40 will indicate a change in salinity between the point responsible for that reading and the calibration point.

The output from the horizontal polarization detector 30H is also inputted to a multiplier 50, which can be conventionally embodied as a resistance device, operational amplifier or some other conventional apparatus.

Another input to the multiplier 50, representing the magnitude by which the input from the horizontal detector is to be multiplied, comes from a voltage divider network 60 consisting of a potentiometer 65 and 2 DC voltage sources 70, 75, arranged as shown in FIG. 1. The potentiometer is, in the preferred embodiment, implemented as a tunable dial whereby the signal amplitude fed into the multiplier 50 can be adjusted from a negative to a positive value.

Figure 2:
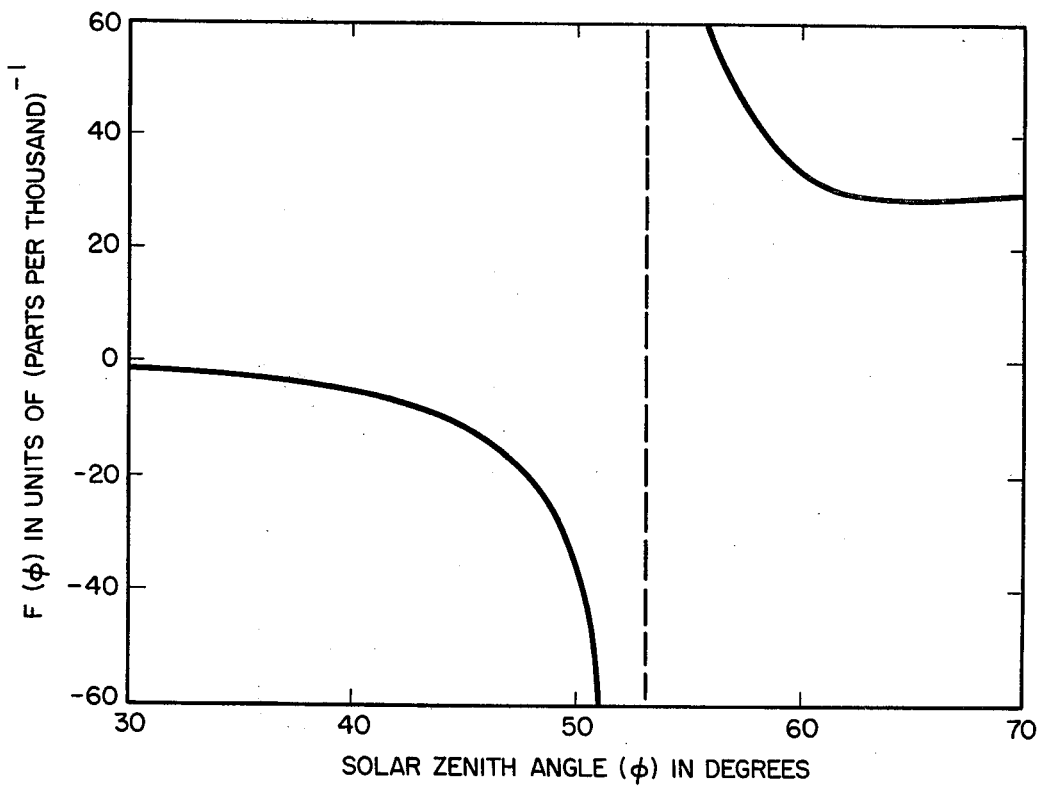
FIG. 2 is a graph showing a function of the solar zenith angle $f(\phi)$ plotted against the solar zanith angle $\phi$ in degrees.

The actual value which is to be inputted to the multiplier 50 from the voltage divider network 60 is a linear function of the function $f(\phi)$ of the solar zenith angle $\phi$ shown in FIG. 2. The solar zenith angle, i.e., the angular separation of the sun from the zenith, is readily measurable or can be obtained from tables, since it is merely a function of latitude, data and local time. The instrument is, then, adjusted for the particular solar zenith angle by adjusting the voltage divider network 60 (for example by properly turning a dial, in the manner of tuning a radio) so that the proper value of $f(\phi)$ is inputted to the multiplier 50.

The two inputs are analog multiplied by the multiplier 50 and the product is outputted.

An analog divider 80 which in the preferred embodiment comprises an ordinary resistance divider network or similar division element, receives the output from the multiplier 50 and the subtractor 40. Here, the difference from the subtractor is divided by the product from the multiplier and an output representing this quotient is generated. This output may be displayed and read by means of an ordinary volt meter 90 or an oscilloscope, a stripchart recorder, a digital display or any other conventional readout device.

I have found that if the instrument is calibrated so that the subtractor 40 outputs a null signal corresponding to a remote point of known salinity and at a later point the output from the horizontal detector is multiplied by $f(\phi)$ and this product is divided into the difference between the output from the horizontal and vertical detectors at that point, the quotient is a linear function of the difference in salinity between that point and the calibration point. The actual linear function is dependent only on the calibration of the various elements in the instrument. Therefore, by simply calibrating the output device 90, the latter can be made to generate a reading of the salinity difference itself for all measurements.

Thus, the present invention provides an instrument whereby after a simple calibration, the difference in salinity between a given point and a previous calibration point can be read directly from a volt meter or other display device without the necessity of a computer or other numerical processing means.

While the curve in FIG. 2 representing $f(\phi)$ versus $\phi$ will be sufficiently precise for most applications, in certain circumstances, the value obtained from this curve may not prove to be sufficiently accurate. For the latter purpose it might be advisable to produce a table of values of $f(\phi)$ versus each incremental value of the solar zenith angle $\phi$. For this purpose, it will be necessary to generate actual values from the following equation:

$$f(\phi) = \frac{\delta \rho_H}{\delta S} \left| + \frac{\rho_V}{\rho_H} - \frac{\delta \rho_V}{\delta S} \right| + \frac{\rho_H}{\rho_V}$$

where:
$\phi$ = solar zenith angle,
$\rho_H$ = reflectivity of the horizontally polarized radiation,
$\rho_V$ = reflectivity of the vertically polarized radiation, and
S = salinity,
where $\rho H$ and $\rho v$ may be obtained from the well known Fresnel equations.

Figure 3:
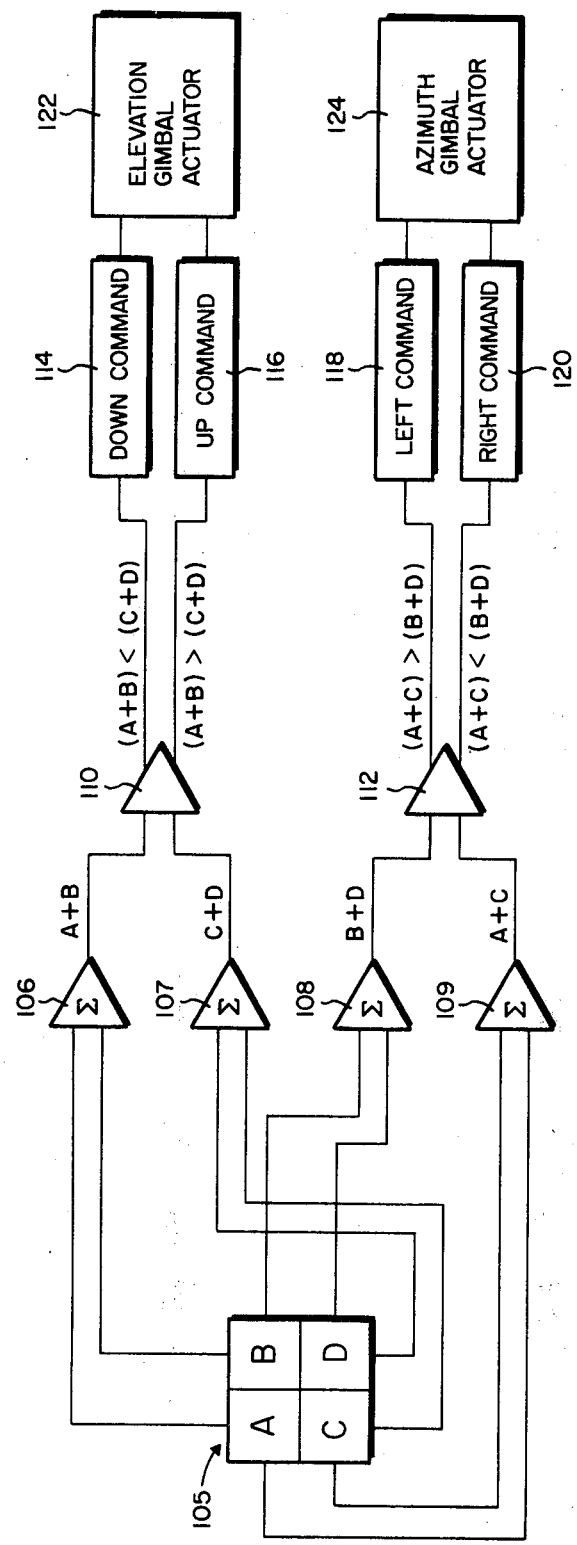
FIG. 3 is a schematic representation of the preferred apparatus utilized in directing the senor of the present invention for solar glitter pattern tracking.

The axis (axes, in the illustrated preferred embodiment) of the optical sensor of the present invention must always be pointed, with reasonable accuracy, at the center of the glitter pattern, so that true specular reflection readings may be obtained. This requires that some sort of sensor pointing apparatus be employed. While numerous means could be employed, a workable apparatus is shown schematically in FIG. 3.

Here, an array of four photodetectors is arranged in quadrants numbered A, B, C and D. Optical means not shown causes a light beam from the solar glitter pattern on the ocean surface to be focused onto the array. This light beam is parallel to the beam received by the primary optical sensor apparatus. This can, of course, be accomplished by rigid parallel mounting of the optical sensor and the pointer.

In order for convenience in describing the operation of the detector array 105, one must view the array shown schematically in FIG. 6 as if the viewer were behind the array looking toward the glitter pattern on the opposite side.

Assuming each of the detectors is calibrated so that light of a given intensity impinging on any of them will generate the identical output signal amplitude, it follows that if the signal amplitude for each of the detectors is identical, the intensity of light detected by each is identical. Thus, if an image of a remote light source is focused onto the detector array 105 in such a manner that the output signal amplitude from detectors A, B, C and D is identical, it may be safely assumed that if the light source subtends a relatively small angle at the sensor, the sensor is locked onto the center of the light source. If this were not the case, at least one of the detectors would generate a lower output signal amplitude since it would be viewing an edge of the pattern or a region outside the pattern while at least one of the others would be more wholly saturated by light from within the pattern.

Specifically, if the output from detectors A and B together is greater than that from C and D, the detector array 105 is pointed too low, i.e., the image focused onto the upper detectors comes from a region more wholly within the remote light pattern than that focused onto the lower detectors which originate in the region below the pattern. The indicated corrective action would be to tilt the sensor slightly upward so that the lower detectors receive as much light as the upper detectors.

Likewise, if the left detectors A and C receive more light than the right detectors, B and D, the sensor is aimed too far to the right of the remote light source being sensed, and the corrective action would be to tilt the sensor somewhat to the left until both sides receive the same amount of light.

Thus, a remote light pattern can be tracked simply by insuring that detectors A and B receive the same amount of light as detector C and D (for vertical control) and detectors A and C receive as much light as detectors B and D (for horizontal control).

Accordingly, the tracking sensor of the present invention comprises optical means for imaging the remote light source onto the detector array 105 and gimbal actuator means operating in response to the output of the detectors A, B, C and D the array in such a manner that the housing for the tracking sensor (ordinarily a satellite or a portion of it) may be continuously oriented so that the image is centered within the detector array.

To accomplish vertical stabilization, the outputs from detectors, A and B are summed by a summing amplifier 106, and the outputs from detectors C and D are summed by another summing amplifier 107. The outputs from the two summing amplifiers are fed into a comparator 110 which determines whether the sum of the outputs from detectors A and B is greater or less than the sum of the outputs from detectors C and D. If the sum from A and B is less than the sum from C and D, this indicates that the tracking sensor is aimed too high, and a down-command means 114 is actuated to generate an appropriate command to the elevation gimbal actuator 122 for corrective action in orienting the tracking sensor housing.

Horizontal corrections are made by causing the outputs of detectors B and D to be summed by a summing amplifier 108, and the output from detectors A and C to be summed by another summing amplifier 109. A comparator 112 determines whether the sum from A and C is greater or less than the sum from B and D. If it is greater, the tracking sensor is tilted too far to the right of the remote source, and a corrective left command to the azimuth gimbal actuator 124 is generated by the left command means 118. On the other hand, if the sum from A and C is less than the sum from B and D, the azimuth gimbal actuator is commanded by the right command means 120.

Of course, means must be provided to insure that the image of the remote light pattern is focused somewhere within the detector array 105. There are a number of ways of accomplishing this which are familiar to those skilled in the satellite navigation art. One is, of course, to provide an optical apparatus with a field of view of sufficient width to encompass the entire solar glitter pattern and some of the surrounding territory.

In an alternative means of tracking the light pattern, the tracker is made to point at the sun instead of the light pattern, by the method described. The salinity instrument is caused to point a certain angle below the sun, said angle being equal to $\pi-\phi$ (where $\phi$ is the solar zenith angle). In this position, the instrument will be pointing directly at the center of the solar glitter pattern.

I claim:

1. In a method of remotely determining the degree of salinity of water at a specified point at the surface of a body thereof, the steps of:
   a. electro-optically generating a first data signal representative of a first value, corresponding to the intensity of at least a finite wavelength band of the horizontally polarized component of sunlight specularly reflected from a solar glitter pattern at the specified point;
   b. electro-optically generating a second data signal representative of a second value, corresponding to the intensity of at least said finite wavelength band of the vertically polarized component of sunlight specularly reflected from the solar glitter pattern at the specified point;
   c. electronically operating on said first data signal and said second data signal to compute the difference between the first value and the second value;
   d. electronically operating on said first data signal to compute the product of the first value and the value of a particular function of the solar zenith angle at the specified point, said particular function being a linear function of $f(\phi)$ where:

$$f(\phi) = \frac{\delta\rho_H}{\delta_s}\left[1 + \frac{\rho_V}{\rho_H}\right] - \frac{\delta\rho_V}{\delta_s}\left[1 + \frac{\rho_H}{\rho_V}\right],$$

$\phi=$ the solar zenith angle,
$\rho_H =$ reflectivity of the horizontally polarized radiation,
$\rho_v =$ reflectivity of the vertically polarized radiation, and
$s =$ salinity; and
   e. electronically computing the ratio of the difference to the product, whereby a final data signal is generated, said final signal representative of the difference in salinity between said specified point and a particular calibration point at the surface.

2. The method as recited in claim 1, wherein said steps of generating each comprising the steps of:
   a. optically receiving light projected from the glitter pattern;
   b. causing at least a finite wavelength band of the received light to impinge on detector means adapted to generate an electrical signal whose instantaneous amplitude represents the instantaneous intensity of the impinging light; and pl c. converting said electrical signal to said data signal.

3. The method as recited in claim 1, further including the step of calibrating the second data signal, so that the difference corresponding to said particular point at the surface is zero.

4. In an apparatus for remotely determining the degree of salinity of water at a specified point at the surface of a body thereof, the combination comprising:

a. first electro-optical means for generating a first data signal representative of a first value, corresponding to the intensity of at least a finite wavelength band of the horizontally-polarized component of sunlight specularly reflected from a solar glitter pattern at the specified point;
   b. second electro-optical means for generating a second data signal representative of a second value, corresponding to the intensity of at least a finite wavelength band of the vertically-polarized component of sunlight specularly reflected from the solar glitter pattern at the specified point;
   c. first electrical means for operating on said first data signal and said second data signal to compute the difference between the first value and the second value;
   d. second electrical means for generating a third data signal representative of a linear function of $f(\phi)$, where:

$$f(\phi) = \frac{\delta\rho_H}{\delta_s}\left[1 + \frac{\rho_V}{\rho_H}\right] - \frac{\delta\rho_V}{\delta_s}\left[1 + \frac{\rho_H}{\rho_V}\right]$$

$\phi=$ the solar zenith angle,
$\rho_H =$ reflectivity of the horizontally polarized radiation,
$\rho_v =$ reflectivity of the vertically polarized radiation, and
$S =$ salinity;
   e. third electrical means for computing the product of the first data signal and the third data signal; and
   f. fourth electrical means for computing the ratio of the difference to the product, whereby a final data signal is generated, said final signal representative of the difference in salinity between said specified point and a particular calibration point at the surface.

5. The apparatus as recited in claim 4 wherein:
said first electro-optical means comprises detector means adapted to generate an electrical signal whose instantaneous amplitude represents the instantaneous intensity of at least a finite wavelength band of light impinging thereon, optical means to receive light radiated from the glitter pattern and to cause at least the finite wavelength band thereof to impinge on said detector means, and polarizing means intervening between said detector means and said optical means, said polarizing means adapted to pass, substantially unimpeded, the horizontally polarized component of the light radiated from the glitter pattern and to substantially block the vertically polarized component of the light radiated therefrom; and
said second electro-optical means comprises detector means adapted to generate an electrical signal whose instantaneous amplitude represents the instantaneous intensity of at least a finite wavelength band of light impinging thereon, optical means to receive light radiated from the glitter pattern and to cause at least the finite wavelength band thereof to impinge on said detector means, and polarizing means intervening between said detector means and said optical means, said polarizing means adapted to pass, substantially unimpeded, the vertically polarized component of the light radiated from the glitter pattern and to substantially block the horizontally polarized component of the light radiated therefrom.

6. The apparatus as recited in claim 4 further including tracking sensor means operably connected to said first electro-optical means and said second electro-optical means, said tracking sensor means adapted to cause said first electro-optical means and said second electro-optical means to be oriented with respect to the solar glitter pattern in such a manner that the intensity of the light impinging upon said first and second electro-optical means is substantially maximized.

7. The apparatus as recited in claim 6 wherein said tracking sensor means comprises:

electro-optical detector means oriented with respect to the glitter pattern in such a manner as to receive a beam of light reflected therefrom, said detector means adapted to generate a first electrical tracking signal whose instantaneous amplitude is representative of the instantaneous intensity of the upper portion of the beam, a second electrical tracking signal whose instantaneous amplitude is representative of the instantaneous intensity of the lower portion of the beam, a third electicak tracking signal whose instantaneous amplitude is representative of the instantaneous intensity of the leftward portion of the beam, and a fourth electrical tracking signal whose instantaneous amplitude is representative of the instantaneous of the rightward portion of the beam;

electronic means to compare the amplitudes of said first and second electrical signals and to compare the amplitudes of said third and fourth electrical signals, said electronic comparison means adapted to determine by what amount the angular orientation of said detector means must be altered in order to cause the amplitude of said first signal to equal that of said second signal and the amplitude of said third signal to equal that of said fourth signal, and, based on this determination, to generate an electrical command signal representative of said reorientation data; and electro-mechanical means responsive to said reorientation command signal adapted, in response thereto, to reorient said tracking sensor means so that the amplitude of said first electrical signals equals the amplitude of said second electrical signal and the amplitude of said third electrical signal equals the amplitude of said fourth electrical signal, said reorientation means adapted also to reorient said first electro-optical means and said second electro-optical means in such manner that upon reorientation of said tracking sensor detector means, the intensity of light impinging on said first electro-optical means and upon said second electro-optical means is substantially maximized.

8. The apparatus as recited in claim 7, wherein said first electro-optical means and said electro-optical detector are mutually mechanically connected in substantially rigid manner.

* * * * *